United States Patent [19]

Rothman et al.

[11] 4,215,693
[45] Aug. 5, 1980

[54] BIOLOGICAL SURGICAL DRESSING

[76] Inventors: Ulf S. E. Rothman, V. Mellauv 2, Höllriksaas; Sven C. Frederiksen, Rabäcksgatan 5; Bernt O. Leube, Almlyckegränd 5, both of Malmö, all of Sweden

[21] Appl. No.: 887,701

[22] Filed: Mar. 17, 1978

Related U.S. Application Data

[63] Continuation of Ser. No. 706,426, Jul. 19, 1976, abandoned.

[30] Foreign Application Priority Data

Aug. 7, 1975 [CH] Switzerland ............... 10344/75

[51] Int. Cl.² ............................................. A61F 13/00
[52] U.S. Cl. ................................. 128/296; 106/124; 260/117
[58] Field of Search ....................... 128/155–156, 128/296, 285, DIG. 8, 325; 260/117; 106/124–125

[56] References Cited

U.S. PATENT DOCUMENTS

| 2,525,753 | 10/1950 | Yutzy et al. | 260/117 |
|---|---|---|---|
| 2,557,871 | 6/1951 | Harnack et al. | 260/117 |
| 2,610,625 | 9/1952 | Sifferd et al. | 128/296 |
| 3,157,524 | 11/1964 | Artandi | 128/296 |
| 3,368,911 | 2/1968 | Kuntz et al. | 128/296 |
| 3,587,586 | 6/1971 | Kronenthal | 128/296 |

Primary Examiner—Robert W. Michell
Assistant Examiner—C. F. Rosenbaum
Attorney, Agent, or Firm—Ladas & Parry

[57] ABSTRACT

A biological surgical dressing, especially a surgical dressing for wounds composed of a combination of collagen fibers and carbamide, primarily in a ratio of 65 to 99 percent by weight collagen fibers and 1 to 35 percent by weight carbamide.

9 Claims, No Drawings

BIOLOGICAL SURGICAL DRESSING

This is a continuation, of application Ser. No. 706,426 filed July 19, 1976 and now abandoned.

BACKGROUND OF THE INVENTION

The present invention relates to a new and improved biological surgical dressing, especially a surgical dressing for wounds, formed on the basis of collagen fibers.

It is known in surgery that it is possible to use collagen in different forms, such as film, powder or collagen fiber gauze, especially for stilling bleeding. Fabrication of collagen fiber gauzes or fabrics, especially for use as a biological surgical dressing, is disclosed for instance in French Pat. No. 1,441,817 and in the Swedish Pat. No. 346,910, which describe the manufacture of collagen fiber gauzes or fabrics in the form of felt-like membranes or sponge-like layers.

The heretofore known collagen fiber gauzes and other collagen materials are associated with certain drawbacks. Thus, the prior art collagen materials are not expansible and do not participate in the movements which normally arise at the skin, rather become taut and resist such skin movements which cannot be avoided during the normal movements of the body of a patient.

Additionally, the state-of-the-art collagen materials have added thereto a softening additive in order to be able to be processed and to insure that the fabricated collagen fiber gauze is sufficiently soft and pliable.

Moreover, the known collagen fiber gauzes or fabrics adhere poorly or not at all to wet surfaces, such as wounds which excrete liquid.

SUMMARY OF THE INVENTION

Hence, it is a primary object of the present invention to provide a physiologically compatible, biological surgical dressing which possesses styptic properties as well as properties protecting against external infections, is adherent to wet surfaces, permits the passage of gases and liquids, at the same time is elastic and during movements of the body does not draw the skin and, without the addition of softening agents, remains extremely soft and pliable.

The biological surgical dressing of this invention, which possesses the above-indicated properties, is a dressing material, especially a dressing material for wounds, formed on the basis of collagen fibers. It is characterized by the combination of collagen fibers and carbamide, especially 65 to 99 percent by weight collagen fibers and 1 to 35 percent by weight carbamide. The surgical dressing of the invention preferably consists of 80 to 95 percent by weight collagen fibers and 5 to 20 percent by weight carbamide.

It has been proven that the addition of carbamide within the above-described limits renders the collagen fiber material especially suitable as surgical dressing. The carbamide possesses the characteristic of extracting moisture from the air, so that the collagen fiber material remains soft and elastic and without resistance and without stretching the skin follows the movement of the skin. In any event it replaces or reduces the need for other softening agents and imparts to the collagen fiber material an adhesion, which not only prevents the repulsion of the liquid emanating from the wound, but in fact remains adhering to such wound location while absorbing the eliminated liquid.

The collagen fiber material which is present in the biological surgical dressing of the invention is preferably obtained from animals, such as the skin and tendons of cattle in particular. According to a certain technique it is contemplated in order to obtain the collagen fibers from such material to subject the raw stock or material to an alkaline swelling, for instance in calcium hydroxide solution, followed by washing and acid treatment, such as with hydrochloric acid, whereafter the swelled and cleaned material is converted into a fiber form by mechanical splitting and possibly formed into a coherent layer and dried.

In this manner there is obtained a pure and nondenaturized collagen fiber material which is free from antigenicity and at the same time retains without change its original advantageous properties.

The collagen fiber material is combined with carbamide in a quantity of 1 to 35 percent by weight. Quantities of carbamide smaller than about 1 percent by weight do not show any appreciable effect and if the carbamide content exceeds approximately 35 percent by weight then the combination becomes hypertone.

It is known that carbamide normally is present in the skin and due to its hygroscopic properties increases the moisture content of the skin and also that it possesses a slight local anesthetic effect and is weakly bacteriostatic. Salves are therefore admixed to the carbamide.

It was not known and is a new and completely surprising effect that if carbamide is admixed with collagen fiber material the latter becomes pliable and it allows following the movements of the skin at which there has been applied a layer of carbamide-containing collagen fiber material.

The collagen fiber material and the carbamide are most advantageously combined such that the collagen material is immersed in a carbamide solution in the form of a film or the like. For instance, the collagen fiber film can be immersed in a 10 percent carbamide-aqueous solution for 3 minutes and thereafter dried. By varying the carbamide content in the solution and the immersion time it is possible to regulate the desired quantity of carbamide taken-up by the collagen material. A drying time of about 4 hours at approximately 30° C. is satisfactory.

The carbamide-containing collagen material according to the invention, and most advantageously formed into band- or sheet-like layers, provides an exceptional physiologically compatible, biological surgical dressing having a pronounced styptic effect. Further, due to its bacteriostatic activity it protects against external infections, adheres to wet wound surfaces, and permits the passage of liquids and gases. It is elastic, follows the movements of the skin situated below the dressing, there is no stretching of the wound, possesses good softness, even without the addition of special softening agents, but this does not however preclude the possibility of further increasing the softness in that there are added special softening agents, such as glycerol, polyethylene glycol or propylene glycol.

The biological surgical dressing of the invention can be used for many different applications in medicine. Thus, it can be employed in the form of a film or the like for the treatment of burns or cauterized wounds in that, the wound surface is covered with the above-described material and it is thereby protected against further injury and/or infection. In order to prevent infection of the wound it is possible, according to the invention, to add to the surgical dressing therapeutically effective materials, such as for instance cortisone, penicilin or other antibiotics, analgesics, antibodies, compounds which retard or promote the coagulation of blood, or radioactive isotopes, in order to thus obtain many different effective collagen fiber dressings or gauzes.

At the present time in the event of a burn there is oftentimes used thin layers of pig skin in order to cover and protect the oftentimes large surface of the wound. However, the pig skin cannot be completely freed of contaminants, such as pig's blood, and thus oftentimes can produce allergies. The surgical dressing of the invention, wherein the collagen fiber material is produced in the manner described above, provides an extremely good substitute for pig skin, since it is a biological material free of contaminants which does not cause any allergies, adheres extremely well to wet surfaces, protects the wound surface against external infections and effectively promotes the healing and forming of new skin.

The surgical dressing of the invention can be successfully employed for the provisional covering and protection of wounds prior to an operation.

It can be used extremely well for the treatment of moist, exuding eczema in that it absorbs or passes the exuded liquid and, additionally, remains adhering extremely well to the exuding wound.

The surgical dressing of the present invention can be beneficially employed as a plaster or bandage, as a styptic or blood-stilling pad on plasters or as plaster carriers, most advantageously in combination with an adhesive substance. It is useful in order to still the coagulation of blood in the cavities of the body such as for instance in the extraction cavity following extraction of a tooth and it possesses the advantageous property of being dissolved in the body liquid and for this reason can be employed at such locations where difficulties exist of subsequently removing the same.

The invention will be further explained on the basis of the following Examples, wherein Example 1 demonstrates the preferred mode of manufacturing a collagen film constituting the basis of the biological surgical dressing. Examples 2 to 4 illustrate certain properties of the collagen film and Examples 5 to 13 illustrate different fields of application of the biolgical surgical dressing.

EXAMPLE 1

Such demonstrates the manufacture of a collagen film which is used in the subsequent Examples.

Pieces of cow skin are immersed in cream of lime or lime milk and brought to a pH of 13. After swelling of the skin pieces such are washed with water and brought to a pH of 8. Thereafter, the skin pieces are placed in a diluted hydrochloric acid solution until reaching a pH of 2.5 to 4.0. The thus treated, markedly swollen skin pieces are then rolled and fed a number of times through sieves having a hole diameter of 1.5 to 1.0 mm, whereby the skin pieces have imparted thereto the desired fiber shape. By pressing the material there is obtained a film of desired strength.

EXAMPLE 2

Collagen film produced according to Example 1, with a thickness of 0.85 mm during swelling in a 0.9 percent aqueous solution of NaCl, was examined with regard to its hydrophilic properties. Small pieces of film of 1 cm$^2$ were immersed in distilled water and in solutions of carbamide, glycerol and both carbamide as well as glycerol in distilled water during a period of 12 hours. The samples thereafter were dried on filter paper and placed in a glass chamber having a specific relative humidity. In the chamber there was maintained a relative humidity of 86 percent in that a large Petri dish containing sodium tartrate was placed into the chamber. The water content of the samples was measured after 6 hours of incubation in the chamber by weighing the same on a torsion balance and weighing was repeated after the samples were exposed for 24 hours to dry air. The hydrophilic or water-absorbing properties were expressed in terms of the weight difference in percent of the dry weight of the samples. The obtained results are listed in Table 1.

Table 1

| Treatment | Water Absorption in Percent of the Dry Weight at 86% Relative Humidity |
| --- | --- |
| Distilled water | 9.8 |
| 5% Carbamide | 12.7 |
| 10% Carbamide | 16.2 |
| 20% Carbamide | 27.0 |
| 30% Glycerol | 15.3 |
| 30% Glycerol + 20% Carbamide | 21.0 |

The result proved that a carbamide-containing collagen-film possesses a surprisingly large water absorption and water storage capacity.

EXAMPLE 3

Thin collagen layers, as produced by Example 1, were examined with respect to their water absorption capability. Gamma sterilized (2.4 M Rad) collagen film was immersed for 1 minute in the following respective liquids with the following results:

Table 2

| Solution | Absorption capability (x original dry weight) |
| --- | --- |
| 0.9% NaCl | 4.81 |
| Distilled water | 9.08 |
| 10% Carbamide W/v | 8.60 |
| 20% Carbamide W/v | 8.66 |

The result confirmed the already known fact that non-denaturized, slightly cross-linked collagen has its greatest swelling capability in a salt-free environment. A carbamide-containing milieu according to this invention only reduces to a slight degree the swelling capability.

EXAMPLE 4

This Example describes the styptic properties of the collagen film.

A thin-walled collagen film having a liquid-absorption capability of 0.02 grams of a 0.9 percent aqueous solution of NaCl/cm$^2$ was immersed for 3 minutes in a 10 percent (w/v) carbamide solution. Thereafter, the film was exposed for 4 hours to dry air at a temperature of 28° C. A sample strip having a dimension of 1×3 cm was introduced into a vitreous test tube containing 5 ml citrate blood. After 5 minutes of shaking the test tube there was microscopically examined the thrombocyte content in the blood. In this manner it was possible to confirm that the collagen film had reduced the thrombodyte content of the blood to 1/10 of the original value. For comparison purposes there was examined in the same manner the blood coagulating activity of oxidized cotton (commercially available under the trademark "SURGICEL" from Johnson & Johnson, New Brunswick, N.J., USA as well as gelatin sponge sold under the mark "SPONGOSTAN," by Ferrosan, AB, Malmö, Sweden) and there were measured the corresponding values of 6/10 and 5/10 respectively.

A collagen film which was not cross-linked and to which there was added carbamide, possesses according to these results exceptional blood coagulating properties since the thrombocytes in the blood exhibit an affinity for the collagen fibrilles of the film. In this regard the thrombocytes release adenosine diphosphate which initiate the coagulation process.

EXAMPLE 5

A dog weighing 15 kilograms was anesthetized with "NEMBUTAL," a trademark product of Abbot Laboratories, USA. After opening the stomach incision wounds were made in the liver, leading to intense bleeding. Collagen film, produced in the manner of Example 1, was placed over the bleeding surface, and impregnated with carbamide solution as in Example 4. Due to the exceptional adhesion of the material at exuding and bleeding surfaces the film remained fixedly adhering at the applied location and bleeding stopped after 4 minutes. For comparison purposes also a gelatin sponge ("SPONGOSTAN") was applied to a correspondingly cut surface. The bleeding pressure rapidly removed the sponge, and therefore the same had to be sewn, resulting in a further loss in blood. Several days later the dog again was anesthetized and the place where the operation was performed was inspected. The stomach cavity was free of bleeding. The collagen film had spontaneously dissolved and the wound healed. The gelatin sponge only lost very little of its size.

EXAMPLE 6

After a tooth extraction in the upper jaw of a 42 year old man bleeding developed which could not be stopped with a gelatin sponge tampon, because notwithstanding repeated application such always was forced out of the extraction cavity.

Now the bleeding cavity was tamponaged with collagen film produced according to Example 1 and impregnated with carbamide as in Example 4. Bleeding stopped after 5 minutes and the tampon was still firmly in place after 24 hours. The wound cavity was satisfactorily healed after an additional 4 days, without any sign of an inflamation reaction.

EXAMPLE 7

A 35 year old woman who had a cold developed a strong nose bleed at the right side which could not be stopped by means of the usual external compression of the nose.

Collagen film, produced as in Example 1 and impregnated with cabamide solution as in Example 4, was applied in the nostrils and compressed for 2 minutes. Bleeding stopped and the film remained fixed in place for 2 days notwithstanding the nose secretions which occurred at the patient due to infection of the upper air passageway.

EXAMPLE 8

In conjunction with surgical removal of the uterus of a 31 year old woman, uncontrolled bleeding followed the operation, notwithstanding the application of tampons with compression. The latter were removed and replaced by 5 grams collagen film, produced as in Example 1 and impregnated with carbamide solution as in Example 4, and gamma-sterilized with 2.4 M Rad. Prior to application the film was moistened with 0.9 percent NaCl. Bleeding stopped after a few minutes.

EXAMPLE 9

Collagen film, fabricated in accordance with Example 1, was admixed for 5 minutes with a solution consisting of 20 percent (W/v) carbamide, 5 percent (W/v) lactic acid, 4.5 percent (W/v) betaine and "TWEEN 20." Thereafter, the material was dried for 4 hours in dry air at 30° C. and packaged into suitable size under vacuum conditions. The packages then were gamma-sterilized. In this way there was obtained, already in dry condition, an extremely soft and formable foil possessing moisture-preserving properties, and which can be used for the skin and open wounds. After the material, following slight initial moistening with isotonic sodium chloride solution, was applied to dry undamaged skin surfaces as surgical dressing, it retained for 6 days its softness and shapability. During the entire application time the material remained sufficiently adherent with respect to the skin surfaces located therebelow, without exhibiting such macerations and irritations of the skin which can oftentimes be observed when using bandages having an adhesive mass. The above-described physiologically compatible dressing of the invention can be removed at any time and without pain or discomfort by wetting with water. In comparison there was also examined a collagen film without softness- and moisture-preserving carbamide additive. In this case there could be detected a decisive difference, since such material dried out and shrunk together within a few hours at the surface of the skin, leading to stretching and creasing or folding of the skin.

EXAMPLE 10

The following Example demonstrates the advantage of the surgical dressing of the invention when it is used in conjunction with a therapeutic effective substance.

Thin-wall collagen film was produced in the manner described in Example 9, but however 10 grams of dry foil were admixed with a solution of the following content:

| | |
|---|---|
| Hydrocortisone | 0.5% w/v |
| Propylene glycol | 10.0% w/v |
| "TWEEN 20" | 2.0% w/v |
| Ethanol | 10.0% w/v |
| Carbamide | 20% w/v |
| Lactic acid | 4.5% w/v |
| Betaine | 4.5% w/v |

The thus treated collagen film had a pH of 3.5.

A 74 year old woman with a markedly exuding eczema at the shank of the leg and about the size of a hand, was treated by daily application of the collagen film heretofore described. At all times the material possessed good adhesion at the eczema surface and the hydrocortisone was continually therapeutically effective under maximum conditions. After 4 days the eczema was healed without pain.

EXAMPLE 11

As a result of a traffic accident a 31 year old man received gash- and superficial wounds at the thumb and index finger of the left hand. The deeper wounds were saturated in conventional manner, whereafter both fingers were bandaged with material as described in Example 8 and without the use of additional external surgical dressings. The material was removed after 5 days and the outer wound locations were completely healed. Particularly advantageous was the absence of blood residues between the dressing and the wound, brought about by the styptic properties of the material.

EXAMPLE 12

During plastic surgery skin was removed from the front side of the right shank of the leg of a 40 year old man to a thicknes of 0.5 mm. As a consequence thereof there occurred the normal oozing of blood at a surface of 7×20 cm. Collagen film, as fabricated in Example 9, was applied as the single dressing. Bleeding stopped spontaneously and without compression after 5 minutes, and the blood coagulant below the film could be pressed out without restarting bleeding. The wound surface then could be inspected each day due to the transparency of the material. After the expiration of 9 days the dressing could be removed without pain from the completely healed wound. During the entire treatment time the material retained its softness and elasticity and allowed mobilization of the patient already after a few days following the operation.

EXAMPLE 13

A 57 year old man received a deep burn from an open flame at the front side of the torso. After treatment for 14 days with the usual exposure of the burned body portions in dry air it was determined that the skin was completely de-vitalized and the thick scab which formed at the wound had to be removed in order to eliminate any danger of infection. As the wound scab was removed with an anesthetic considerable bleeding occurred. Collagen film, as produced according to Example 9, was applied to the burn as the single dressing and good stilling of the blood was achieved. Since the material was exchanged each third day over a period of 2 weeks it was possible to obtain a satisfactory infection-free so-called granulation surface, which could be transplanted with success.

This Example indicates the applicability of the material for artificial skin, at those locations where skin is completely missing, in order to protect against the danger of infection and increased loss of moisture. Another advantage in this case is the semi-permeable characteristic of the collagen film, permitting of a certain passage of gases and liquid through the material.

Having now discussed in considerable detail illustrative and preferred embodiments of the invention, it should be apparent that the objects set forth at the outset of this specification have been satisfied. Accordingly,

What is claimed is:

1. A biological surgical dressing, especially a surgical dressing for wounds, comprising a combination of collagen fibers and carbamide, there being present 65 to 99 percent by weight collagen fibers and 1 to 35 percent by weight carbamide.

2. The surgical dressing as defined in claim 1, wherein the collagen fibers are present in an amount of 80 to 95 percent by weight and the carbamide in an amount of 5 to 20 percent by weight.

3. The surgical dressing as defined in claim 1, wherein the surgical dressing is in the form of a film.

4. The surgical dressing as defined in claim 1, wherein the surgical dressing is in the form of a foil.

5. The surgical dressing as defined in claim 1, wherein the collagen fibers of the surgical dressing consist of animal material.

6. The surgical dressing as defined in claim 5, wherein the animal material is the skin of an animal.

7. The surgical dressing as defined in claim 5, wherein the collagen fibers of animal material are obtained by subjecting the animal material to alkaline swelling, washing and acid treatment, and transformation of the thus swelled and cleaned material into fibers by mechanical splitting and drying of such material.

8. The surgical dressing as defined in claim 7, wherein the alkaline swelling is accomplished with lime milk.

9. The surgical dressing as defined in claim 7, wherein the acid treatment is accomplished with hydrochloric acid.

* * * * *